United States Patent [19]

vonReis et al.

[11] Patent Number: 4,459,139

[45] Date of Patent: Jul. 10, 1984

[54] DISPOSABLE FILTER DEVICE AND LIQUID ASPIRATING SYSTEM INCORPORATING SAME

[75] Inventors: Charles E. vonReis; Karlis Vizulis, both of Ann Arbor, Mich.

[73] Assignee: Gelman Sciences Inc., Ann Arbor, Mich.

[21] Appl. No.: 301,501

[22] Filed: Sep. 14, 1981

[51] Int. Cl.³ ............................................. B01D 19/00
[52] U.S. Cl. ........................................ 55/189; 55/159; 210/416.1
[58] Field of Search .......................... 55/158, 159, 189; 128/214 R, 214 C, 283; 210/416.1, 445, 446, 451, 488–490, 492

[56] References Cited

U.S. PATENT DOCUMENTS

| | | | |
|---|---|---|---|
| 3,631,654 | 1/1972 | Riely et al. | 55/159 |
| 3,650,093 | 3/1972 | Rosenberg | 55/159 |
| 3,782,083 | 1/1974 | Rosenberg | 210/445 X |
| 3,854,907 | 12/1974 | Rising | 55/159 |
| 3,882,026 | 5/1975 | McPhee | 128/214 C X |
| 3,952,727 | 4/1976 | Nolan | 128/283 |
| 4,004,587 | 1/1977 | Jess | 55/159 X |
| 4,035,304 | 7/1977 | Watanabe | 210/445 X |
| 4,056,100 | 11/1977 | Noiles | 128/214 C |
| 4,116,646 | 9/1978 | Edwards | 55/159 |
| 4,120,715 | 10/1978 | Ockwell et al. | 128/283 X |
| 4,200,095 | 4/1980 | Reti | 128/214 C |
| 4,225,440 | 9/1980 | Pitesky | 210/445 X |
| 4,274,848 | 6/1981 | La Gro | 128/283 X |
| 4,318,406 | 3/1982 | McLeod | 128/283 |

FOREIGN PATENT DOCUMENTS 1221625 2/1971 United Kingdom ................. 55/159

Primary Examiner—Robert H. Spitzer
Attorney, Agent, or Firm—Reising, Ethington, Barnard, Perry & Milton

[57] ABSTRACT

The disposable filter device of the invention has a housing with a fluid inlet chamber and fluid outlet chamber separated by a hydrophobic filter and having a hydrophilic filter on the inlet chamber side of the hydrophobic filter. In the liquid aspirating system, the disposable filter device is connected between the liquid collection container and the inlet to the aspirator, the hydrophobic filter functioning to prevent the passage of any liquid to the aspirator and the hydrophilic filter functioning to prevent a large accumulation of liquid on the inlet chamber of the filter device and to better assure against any spillage of liquid in the inlet chamber during replacement of the device.

8 Claims, 4 Drawing Figures

DISPOSABLE FILTER DEVICE AND LIQUID ASPIRATING SYSTEM INCORPORATING SAME

TECHNICAL FIELD

The subject matter of the present invention is a filter device which has both a hydrophobic filter and a hydrophilic filter, and an aspirating system, particularly for medical use, incorporating the filter device.

BACKGROUND ART

In surgical and other medical procedures it is frequently necessary to aspirate liquids from the body of the patient. For example, in the case of a patient having a peritoneal infection, it is common procedure to aspirate liquid from the peritoneal cavity. In this and similar cases, it is desirable if not essential to assure that the liquid withdrawn from the patient's body be blocked from entrance to the suction pump or other aspirator. Without such blockage the liquid entering the aspirator can do damage to the aspirator mechanism and, what is worse, any microorganisms in the liquid can not only contaminate the aspirator but also contaminate the atmosphere by way of the exit of such microorganisms from the exhaust port of the aspirator. It is known to fit the inlet conduit of the aspirator with a hydrophobic filter which, because it is hydrophobic, functions to allow the passage of gas but to block the passage of liquid to the aspirator. Further, to assure that no microorganisms reach the aspirator in the air which passes through the hydrophobic filter, it is known to use a hydrophobic filter of sufficiently small pore size to function as a barrier to the passage of the microorganisms through the filter.

In the functioning of such a system it generally occurs over a period of operation that there is an accumulation of liquid in the filter device at the inlet surface of the hydrophobic filter. After continued accumulation, the amount of liquid can be such as to block or at least interfere with the required passage of air through the hydrophobic filter. When this occurs it is necessary to replace the hydrophobic filter device with a fresh one, or at least to empty the device of its accumulated liquid. The latter is disadvantageous in that the liquid is often highly contaminated with microorganisms and hence the emptying of the liquid and reinsertion of the device into the system presents the hazard that the liquid, in the course of being emptied from the device, will give rise to contamination of the ambience by spillage or otherwise. Further, even where the hydrophobic filter device is removed and replaced with a fresh one, if there is any substantial amount of liquid accumulation in the removed device there is the possibility of spillage contamination of the ambience during the removal and replacement procedure.

Hence, while a hydrophobic filter does assure against contamination of the aspirator or the ambience during the period of the efficient function of the hydrophobic filter, there remains the possibility of contamination of the ambience after there has been an accumulation of liquid in the device sufficient to require its replacement or repair.

It is well known that a hydrophilic filter allows the passage of air therethrough until it is saturated with liquid but blocks or at least substantially restricts the passage of air when it does become saturated with liquid. Where the pressure differential across the hydrophilic filter does not exceed the bubble point of the filter (i.e. the pressure required to force air through the filter when it is saturated with liquid), the passage of air is completely blocked when it becomes saturated. But even where the pressure differential does exceed the bubble point, the hydrophilic filter when saturated will nevertheless substantially restrict the passage of air.

DISCLOSURE OF THE INVENTION

The filter device of the present invention has both a hydrophobic filter and a hydrophilic filter, the hydrophilic filter being positioned just upstream of and preferably in contact with the inlet surface of the hydrophobic filter. More specifically, the filter device has a housing with a fluid inlet chamber and a fluid outlet chamber separated by the hydrophobic filter which is sealed to the housing walls, the hydrophilic filter, which is also sealed to the housing walls, being in the inlet chamber adjacent, in overlying relationship to and preferably in contact with, the hydrophobic filter. In operation, as soon as the hydrophilic filter becomes totally saturated with liquid, it blocks or at least substantially restricts the passage of air therethrough to the hydrophobic filter, thereby signaling the need for replacement of the device with a fresh one. At this point there is no great accumulation of liquid in the device, and the amount of liquid which has been accumulated is retained in the device during the replacement procedure by the inherent liquid-retentive characteristics of the hydrophilic filter, largely by reason of its inherent capillary action. Hence, the possibility of contamination of the ambience by the accumulated liquid during the replacement procedure is minimized.

In the preferred embodiment of the invention both the hydrophobic filter and the hydrophilic filter are of microporous membrane and have a pore size rating in air of less than 0.5 microns whereby both membranes function as barriers to the passage of bacteria in the air or aerosols passing therethrough. Other features and advantages will be apparent from the detailed description of a preferred embodiment of the invention which follows.

BEST MODE FOR CARRYING OUT THE INVENTION

Figure 1:
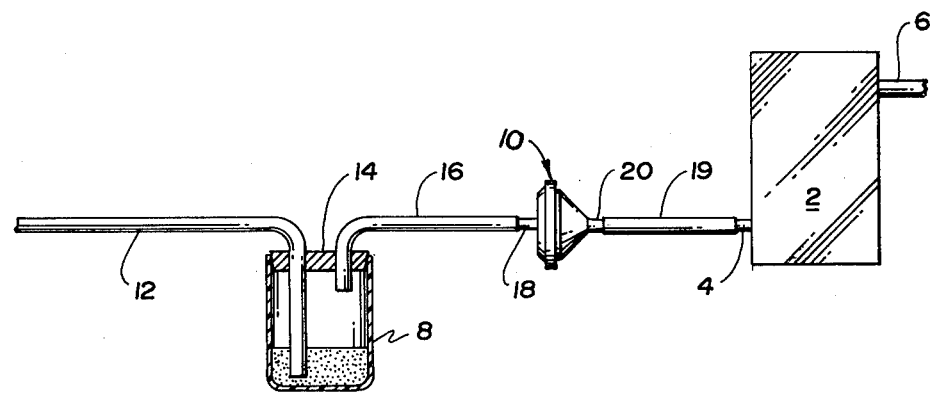
FIG. 1 is a schematic view of an aspirating system embodying the invention.

Referring now to FIG. 1, the aspirating system has an aspirator 2, typically a mechanical suction pump, having an inlet 4 and an outlet 6, a container 8 for the liquid withdrawn from the patient (not shown) and the filter device 10 to be described. A conduit 12 extends from the patient to the bottom of the container through an opening in the sealed lid 14 thereof. Another conduit 16 extends from the top of the container through another opening in the lid thereof to the inlet 18 of the filter device, and the conduit 19 extends from the outlet 20 of the filter device to the inlet of the aspirator. In operation the aspirator pulls a vacuum (i.e. a negative pressure) which extends to the interior of the container so as to aspirate fluid from the patient into the container. The air withdrawn from the container passes through the filter device and into the aspirator where it is exhausted through the outlet port thereof into the ambience. The filter device is to assure that any liquid in the air withdrawn from the container will not reach the aspirator. Normally the air withdrawn from the container contains some of the liquid in aerosol form. Where the liquid contains bacteria, it is normal for the bacteria also to be present in the aerosol which reaches the inlet to the filter device.

Figure 2:
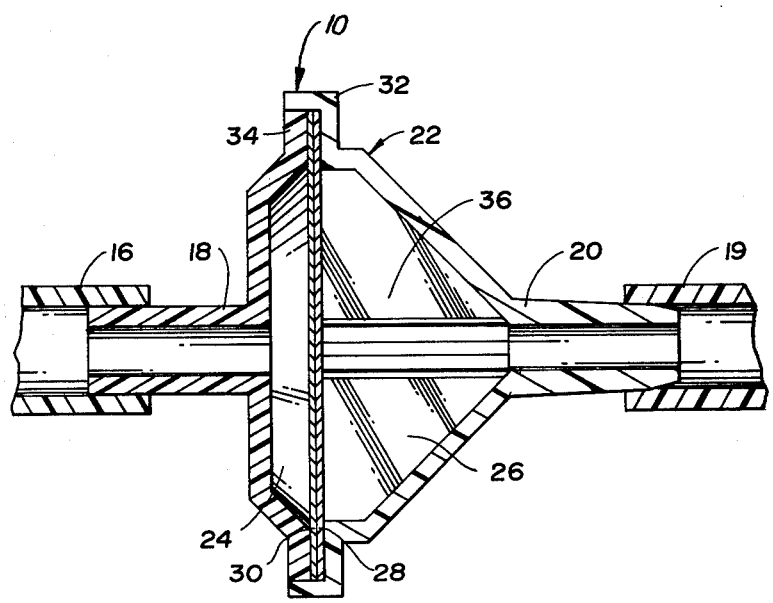
FIG. 2 is a cross sectional view, in enlarged scale, of the filter device in the aspirating system shown in FIG. 1.
Figure 3:
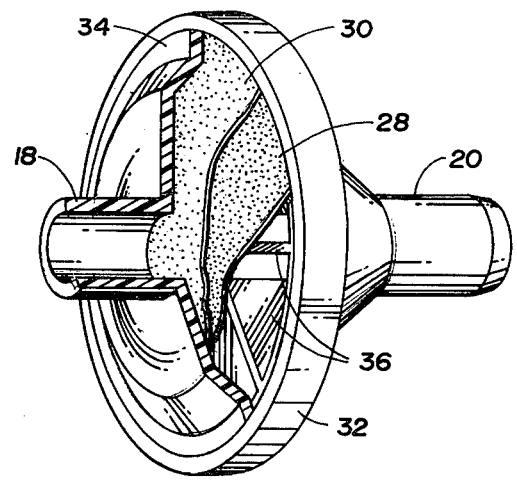
FIG. 3 is a perspective view, with parts broken away, of the filter device shown in FIG. 2.

Referring now to FIGS. 2 and 3, the filter device comprises a housing 22 having an inlet chamber 24 with the inlet opening 18 and an outlet chamber 26 with the outlet opening 20, the chambers 24 and 26 being separated by a hydrophobic filter membrane 28. On the inlet chamber side of the hydrophobic filter membrane is a hydrophilic filter membrane 30 which overlays and is in contact with the hydrophobic filter membrane 28. In the embodiment shown the filter housing, preferably of clear organic plastic, is formed in two parts with annular flanges 32 and 34 which are sealed together with the peripheries of the abutting hydrophobic and hydrophilic filter membranes 28 and 30 therebetween whereby the membranes are sealed to the housing. The housing member which forms the outlet chamber is molded with a plurality of radially extending circumferentially spaced ribs 36 which are in contact with and serve as a support for the hydrophobic filter membrane and hence also for the hydrophilic filter membrane.

The hydrophilic filter membrane should preferably have a pore size rating in air of less than 0.5 microns and can be made of any of the known hydrophilic membrane materials. That marketed by the assignee of the present invention under its trademark Versapor is excellent. This particular membrane is made of a vinyl copolymer with an integral non-woven nylon support and has a pore size rating in liquid of about 1.2 microns but a pore size rating in air of about 0.2 microns. Hence, it blocks the passage of any bacteria in the air passing through it.

The hydrophobic membrane likewise should preferably have a pore size rating in air of less than 0.5 microns and can be of known construction and material for hydrophobic filter membranes. The simplest and most common way to make hydrophobic filter membranes is to start with a hydrophilic membrane and then coat such membrane with a material such as silicone oil to render it hydrophobic. A silicone oil useful for this purpose is that currently manufactured and sold by Dow Chemical Company of Midland, Mich. as a water repellent coating for fabrics and the like. Hence, the hydrophobic filter membrane can be of the aforementioned Versapor membrane but with a coating of the water repellent silicone oil. The key characteristic of the hydrophobic filter membrane is, of course, that it will allow air or other gas to pass therethrough but will block the passage of water or other aqueous liquids. Where the hydrophobic filter membrane has a pore size rating in air of less than 0.5 microns, and preferably about 0.2 microns, it also blocks bacteria from passing therethrough.

Just as a hydrophilic filter membrane has its own bubble point, so a hydrophobic filter membrane has its own water-breakthrough point, i.e. the amount of pressure differential across the membrane required to drive water through it. Where the pressure differential across a hydrophobic filter membrane does somewhat exceed the water-breakthrough point, the filter membrane nevertheless does substantially restrict the amount of water passing therethrough. The hydrophobic filter used in the practice of the present invention should preferably have a water-breakthrough point of at least about 10 psi, and ideally above the maximum pressure differential which can be expected, i.e. about 14 psi for the aspirating system described.

The hydrophilic membrane allows the passage of water or other aqueous liquid therethrough and it also allows the passage of air or other gas therethrough until it becomes saturated, i.e. its pores are filled, with water or other liquid. When so saturated the hydrophilic membrane continues to allow the passage of liquid therethrough but it blocks or substantially restricts the passage of air. The hydrophilic filter membrane used should preferably have a bubble point of at least about 7 psi which is more than 50% of the highest pressure differential that can generally be expected across the membrane in its use in the aspirating system described.

Hence, in the operation of the aspirating system, when the hydrophilic membrane becomes saturated with water it blocks or at least substantially restricts passage of air therethrough. When this occurs, little or no further fluid, either liquid or gas, is drawn into the filter device and hence accumulation of liquid in the inlet chamber does not proceed to where it greatly exceeds that required to totally saturate the hydrophilic filter membrane. This blockage of the filter device by reason of the hydrophilic filter membrane having become saturated with liquid signals the need for replacement of the filter device with a fresh one. The filter device requiring replacement can be readily removed and a new one inserted without any significant hazard or liquid in the device escaping by spillage or otherwise into the ambience of the room. Hence, the filter device and system assure not only against contamination of the aspirator or ambience during operation of the aspirating system but also better assure against contamination of the ambience during replacement of the filter device.

As stated above, it is not essential that the hydrophilic filter membrane totally block the passage of air since with a lesser blockage, as low as 75%, the advantages still obtain. For example, in a preferred embodiment the hydrophilic filter membrane used had a bubble point of from about 7 to 10 psi and as it reached saturation the blockage of air was about 80%, sufficient to indicate the desirability of replacement of the filter device early enough to eliminate or at least minimize the hazard of any spillage of its liquid content.

Figure 4:
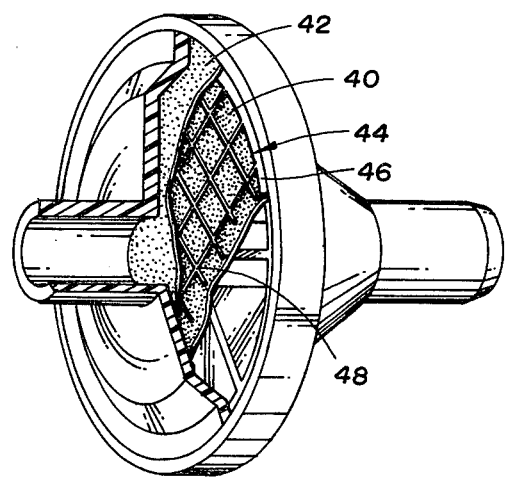
FIG. 4 is a view similar to that of FIG. 2 but showing a modification.

Though preferable, it is not essential that the hydrophilic filter membrane be in contact with the hydrophobic filter membrane. This is illustrated by the FIG. 4 embodiment which is the same as that of FIG. 2 except that the hydrophobic and hydrophilic filter membranes, 40 and 42 respectively, are spaced from each other by a separator 44 in the form of a relatively rigid plastic sheet with a continuous flat periphery 46 sandwiched between the peripheries of the membranes sealed to the housing and with a center portion 48 with openings therethrough, the center portion functioning as a support for the hydrophilic filter membrane.

While the invention has been described specifically with reference to the particular embodiments thereof, various changes and modifications may be made all within the full and intended scope of the claims which follow.

What is claimed is:

1. A disposable filter device comprising a housing with a fluid inlet chamber and a fluid outlet chamber separated from each other by a hydrophobic filter and having a hydrophilic filter in overlying relationship to said hydrophobic filter on the inlet chamber side of the hydrophobic filter such that any fluid flow from the inlet chamber to the outlet chamber can only be by passage of the fluid first through the hydrophilic filter and then through the hydrophobic filter, whereby the flow of liquid from the inlet chamber to outlet chamber is blocked by said hydrophobic filter and whereby the flow of gas from the inlet chamber to the outlet chamber is blocked or at least substantially restricted when the hydrophilic filter is saturated with liquid.

2. A disposable filter device as set forth in claim 1 wherein the hydrophilic filter is in contact with the hydrophobic filter.

3. A disposable filter device as set forth in claim 1 wherein at least one of said hydrophobic and hydrophilic filters has a pore size rating in air of less than 0.5 microns thereby to block the passage of bacteria from the inlet chamber to the outlet chamber.

4. A disposable filter device as set forth in claim 1 or 2 wherein each of said hydrophobic and hydrophilic filters is a filter membrane having a pore size rating in air of less than 0.5 microns.

5. A disposable filter device as set forth in claim 1 wherein the hydrophilic filter has a bubble point of at least about 7 psi and the hydrophobic filter has a water-breakthrough point of at least about 10 psi.

6. A liquid aspirating system for medical use in aspirating liquid from a patient's body, said system comprising an aspirator having a fluid inlet and a fluid outlet, a liquid collection container, a conduit extending from said container for connection to the patient's body, a filter having a fluid inlet and a fluid outlet, a conduit extending from said container to the fluid inlet of said filter, and a conduit extending from the fluid outlet of said filter to the fluid inlet of said aspirator, said filter having a housing with a fluid inlet chamber communicating with the fluid inlet of said filter and with a fluid outlet chamber communicating with the fluid outlet of said filter, a hydrophobic filter membrane separating said fluid inlet and said fluid outlet chambers and having a pore size rating in air of less than 0.5 microns whereby said hydrophobic filter membrane blocks the passage of liquid and blocks the passage of bacteria to said aspirator, and a hydrophilic filter adjacent, in overlying relationship to, said hydrophobic filter membrane on the inlet chamber side of said hydrophobic filter membrane, said hydrophilic filter blocking or at least substantially restricting the passage of gas to said hydrophobic filter membrane when the hydrophilic filter is saturated with liquid.

7. A liquid aspirating system as set forth in claim 6 wherein said hydrophilic filter is in contact with said hydrophobic filter membrane.

8. A liquid aspirating system as set forth in claim 6 wherein said hydrophilic filter is a membrane having a pore size rating in air of less than 0.5 microns and a bubble point of at least about 7 psi and wherein the hydrophobic filter is a membrane having a water-breakthrough point of at least about 10 psi.

* * * * *